United States Patent [19]

Szöke et al.

[11] 3,978,217

[45] Aug. 31, 1976

[54] WATER-SOLUBLE 1 AND/OR 2 ACID ALKYLENE IMIDAZOLES

[75] Inventors: Sándor Szöke, Budapest; György Lugosi, Felsogod; György Csermely; Mária Bakonyi, both of Budapest; Tibor Zsolnai; István Szepessy, both of Debrecen, all of Hungary

[73] Assignee: Chinoin Gyogyszer-es Vegyeszeti Termekek Gyara RT, Budapest, Hungary

[22] Filed: Jan. 30, 1975

[21] Appl. No.: 545,745

[30] Foreign Application Priority Data

Feb. 5, 1974 Hungary............... CI 1440

[52] U.S. Cl.................. 424/245; 260/299; 260/309.2; 424/273
[51] Int. Cl.².................. C07D 235/32
[58] Field of Search........... 260/309.2, 299; 424/273, 245

[56] References Cited
UNITED STATES PATENTS

| | | | |
|---|---|---|---|
| 2,933,502 | 4/1960 | Klopping............... | 260/309.2 |
| 3,574,845 | 4/1971 | Actor et al............. | 260/309.2 |
| 3,657,443 | 4/1972 | Klopping............... | 424/273 |

OTHER PUBLICATIONS
Dranach Chem. Abst. 1972, vol. 77, No. 156075.

*Primary Examiner*—Natalie Trousoe
*Attorney, Agent, or Firm*—Karl F. Ross; Herbert Dubno

[57] ABSTRACT

Compounds of the formula,

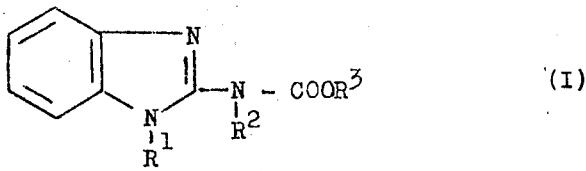

wherein $R^1$ and $R^2$ each stand for hydrogen or a group of the general formula $-(CH_2)_n-SO_3H$, $n$ is an integer between 1 and 5, and $R^3$ stands for an alkyl group, as well as the salts and quaternary salts thereof have been prepared by various methods. The new compounds according to the invention possess valuable fungicidal and/or ovicidal properties, and can be used as active ingredients of plantbiological compositions, cosmetics and pharmaceuticals, respectively.

6 Claims, No Drawings

WATER-SOLUBLE 1 AND/OR 2 ACID ALKYLENE IMIDAZOLES

The invention relates to new water-soluble imidazole derivatives, to plant-biological, cosmetic, ovicidal, fungicidal and pharmeceutical compositions containing the same, as well as to a process for the preparation thereof.

The new compounds according to the invention correspond to the formula

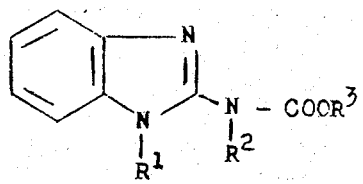

(I)

wherein
R$^1$ and R$^2$ each is hydrogen or a —(CH$_2$)$_n$—SO$_3$H group, but one of R$^1$ and R$^2$ is —(CH$_2$)$_n$—SO$_3$H;
$n$ is an integer between 1 and 5, and
R$^3$ stands for an alkyl group.

The compounds of the formula exist in two tautomeric forms corresponding to the formulee.

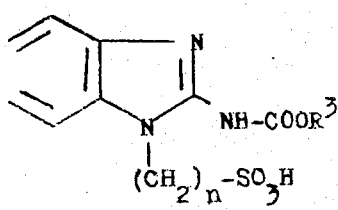

(1a)

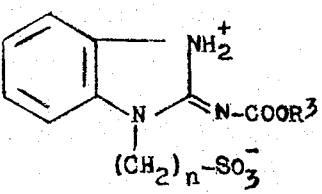

(1b)

All the tautomeric forms and their mixtures, respectively, are included in the definition of compounds of the formula.

As known, the 2-aminobenzimidazoles with an alkylcarbamoyl substituent in position 1 can be applied as fungicidal and/or ovicidal agents (see U.S. Pat. specification No. 3,541,213). Of these known compounds 1-butylcarbamoyl-2-benzimidazolecarbaminic acid methyl ester (Benomyl) is the most important. Investigations on the mechanism of effect of this compound have shown that in aqueous solution it converts very quickly into 2-benzimidazole carbamic acid methyl ester (G.P. Clemons and H.D. Sisler: Phytopathology 59, 705 (1969). It was also found that in plants treated with Benomyl only 2-benzimidazolecarbamic acid methyl ester can be detected. These facts prove the presumption that the actual fungicidal agent is the 2-benzimidazolecarbamic acid methyl ester itself (C.A. Peterson and L.V. Edgington: J. Agric. Fd. Chem. 17, 898( 1969).

The above literature data have also been confirmed by our experiments showing that the fungicidal effect of 2-benzimidazolecarbamic acid methyl ester, in both the spectrum and the grade of activity, is exactly the same as that of 1-butylcarbamoyl-2-benzimidazolecarbamic acid methyl ester. The application of 2-benzimidazolecarbamic acid methyl ester is also advantageous for technical and economical reasons.

Experiments on the technique of application have shown that in ensuring an appropriate fungicidal and/or ovicidal activity it is very important to bring the active agent possibly completely into solution. In some fields of application this is extremely important, since it ensures the optimum contact between the active agent and the seeds or plants. When the active agent cannot be dissolved, special formulations are required. As an example, reference is made to the spray dressing of sowing seeds, which is a recently widespread large-scale operation. With spray-dressing, a more perfect adhesion of the active agent onto the surface of the seeds can be ensured than, for instance, with powder-dressing. Spray-dressing of seeds can be performed with the best results if the dressing agents are readily soluble in water. Other aspects, such as e.g. the economy, the ease of spraying, the need for uniform distribution, good resorption properties, etc. have also directed the attention of research workers towards readily water-soluble fungicidal compositions.

1-Alkylcarbamoyl-2-benzimidazolecarbamic acid alkyl esters, primarily 2-benzimidazolecarbamic acid alkyl esters, are insoluble in water to such an extent, that they can only be used in microcrystalline state, in combination with great amounts of wetting and emulsifying agents, diluents and other additives. In order to ensure minimum inhibitor concentration, the aqueous suspensions are used in combination with surfactants, such as alkylsulfonates, polyglycols, methyl cellosolves, etc. Also, the preparation of the active agent in microcrystalline form involves several technical problems.

This invention is aimed at providing water-soluble derivatives of 2-benzimidazolecarbamic acid alkyl esters which retain or even supersede the activity of the basic insoluble compounds. These water-soluble derivatives can be used with better results and more economically to combat plant mycosis, because they are more readily adsorbed by the plant, and distributed in the plant tissues, thereby entering directly the circulation of the plant tissue fluid, and exert the system fungicidal effect already in low concentrations. Aqueous solutions are also very advantageous in prophylaxis, e.g. in the dressing of seeds or post-emergence spraying of plants.

Now it has been found that the disclosed compounds are excellently water-soluble, and have high biocidal (such as fungicidal, ovicidal, etc.) effects.

The plant-biological effects of the compound prepared according to Example 2 (hereinafter referred to as ABEM-PS) have been examined also by the following tests:

DRESSING OF CORN SEEDS

The germination strength and germinating ability of corn seeds dressed with 0.05 %, 0.1 % 0.15 % by weight of the active agent, respectively, were examined under laboratory conditions. TMTD and Fundazole were used as reference substances. The germination strength was determined 4 days after the beginning of germination, whereas the germinating ability was evaluated on the 6th day. Both the germination strength and germinating ability of the corn seeds dressed with ABEM-PS were satisfactory and similar to those of the seeds dressed with the reference substances.

In the small-parcel experiments 600 corn seeds each, dressed with 0.05 %, 0.1 % and 0.15 % by weight of ABEM-PS, respectively, were sown into four raws of 5 m. length. Also in these experiments TMTD and Fundazole were used as reference substances. ABEM-PS provided positive effect in comparison with the controls, the effectivity being similar to that of the reference substances.

The great-parcel experiments were conducted with OSSK-218 corn seeds dressed with 0.10 % by weight of ABEM-PS. As a reference substance, TMTD was used in the same amount. The number of emerged seedlings increased by 9.73 %/ha., and the crop yield increased by 9.25 %/ha. on the parcels sown with seeds dressed with ABEM-PS in comparison with the results observed on the parcels sown with seeds dressed with TMTD.

DRESSING OF BARLEY SEEDS

When applied onto the seeds, certain fungicides ensure a more or less prolonged protection against powdery mildew during the growth season. This fact has a great practical importance, since the initial infection cannot be detected on the basis of symptoms, thus one might fail to perform the most important preventive treatments.

On the basis of our experiments ABEM-PS proved to be an effective agent in this respect. In the experiments ABEM-PS was applied onto barley seeds in amounts 0.05 %, 0.10 % and 0.15 % by weight, respectively, and the dressed barley seeds were sown in early spring. No other treatment was performed on the crops during the growth season. The rate of powdery mildew infection was evaluated at complete ripening, and the percentage infection was calculated by comparing the number of the healthy and infected leaves, also taking into consideration the thickness of the micelium-deposit appearing on the infected leaves.

In this experiment the infection rate was 40 % for the untreated controls, 23 % for the crops treated with 0.1 % by weight of ABEM-PS, and 26 % for the crops treated with the same amount of Fundazol (reference substance). ABEM-PS did not affect the germination strength and germinating ability of the seeds.

EFFECT AGAINST POWDERY MILDEW ON WINTER WHEAT

Winter wheat crops were sprayed once in the spring with a solution containing 0.05 % or 0.15 % by weight of ABEM-PS, respectively. The protecting effect against powdery mildew was evaluated at complete ripening. The results were expressed as the percentage of the infected leaf surface.

In this experiment the rate of infected leaf surface was 46.2 % for the untreated controls, 16.5 % for the crop sprayed with a solution containing 0.15 % of ABEM-PS, and 14.5 % for the crop sprayed with a solution containing 0.3 % of Fundazol.

PROTECTING EFFECT AGAINST CORN BLIGHT

Corn seeds were germinated for 48 hours on filter paper discs wetted with the substance under examination, thereafter the germinated seeds were infected with a corn blight suspension containing 500 cells per $mm^3$. The seedlings were allowed to grow for 5 days in a chamber of 27°C and 70 % relative humidity, thereafter the percentage number of the infected plants was determined. In this test Fundazol exhibited a complete (100 %) protection in a concentration of 0.2 %, whereas with ABEM-PS complete protection could be achieved already in a concentration of 0.05 %.

Now it has been found that the disclosed compounds are excellently water-soluble, and have high biocidal (such as fungicidal, ovicidal, etc.) effects. When admixed with other active agents or biologically inactive additives, such as carriers, diluents, emulsifying agents, etc., these compounds can be converted into biologically active compositions, such as pharmaceuticals, plant-biological substances, cosmetics, etc.

The invention relates further to a process for the preparation of compounds having the formula or salts or quaternary salts thereof. According to the invention one proceeds as follows:

a. an ester of the formula,

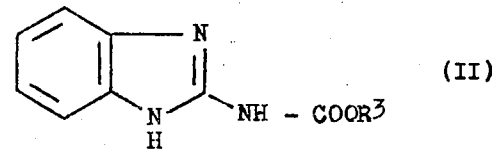

(II)

wherein $R^3$ has the same meanings as given above, is alkylated either with a compound of the formula,

(III)

wherein $m$ stands for an integer of 1 to 3, or with a compound of the formula, $$X - (CH_2)_m - SO_3M \qquad (IV)$$

wherein $m$ has the same meanings as defined above, X stands for halogen, and M stands for hydrogen, sodium, potassium or ammonium; or b. a compound of the formula, $$\underset{\displaystyle \underset{SO_3M}{\overset{\displaystyle \overset{NH_2}{\underset{}{}}}{\bigcirc\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}}}{}} \quad (V)$$

(With $NH(CH_2)_m SO_3 M$ substituent)

wherein m and M each have the same meanings as defined above, is reacted with
1. a diurethane of the formula $$\begin{array}{c} NH-COOR^3 \\ | \\ C-S-CH_3 \\ | \\ N-COOR^3 \end{array} \quad (VI)$$

wherein $R^3$ has the same meanings as defined above, or
2. a thiourea-diurethane of the formula, $$\begin{array}{c} NH_2 \\ | \\ C-S-CH_3 \\ | \\ N-COOR^3 \end{array} \quad (VII)$$

wherein $R^3$ has the same meanings as defined above, or
3. a carboxamidocyanamide of the formula, $$\begin{array}{c} CN \\ | \\ NH-COOR^3 \end{array} \quad (VIII)$$

wherein $R^3$ has the same meanings as defined above, or
4. a dicarboxamidocyanamide of the formula, $$CN-N\begin{array}{c} COOR^3 \\ COOR^3 \end{array} \quad (IX)$$

wherein $R^3$ has the same meanings as defined above, or
5. a carbalkoxyisocyanate of the formula, $$OCN - COOR^3 \quad (X)$$

wherein $R^3$ has the same meanings as defined above, or
6. a carbalkoxyisothiocyanate of the formula, $$SCN - COOR^3 \quad (XI)$$

wherein $R^3$ has the same meanings as defined above, or
7. a dihalomethylene-carbamic acid ester of the formula, $$\begin{array}{c} X \\ \phantom{X}\diagdown \\ \phantom{XX}C=N-COOR^3 \\ \phantom{X}\diagup \\ X \end{array} \quad (XII)$$

wherein $R^3$ and X each have the same meanings as defined above, or
8. a dimethylthiocarbamic acid ester of the formula, $$\begin{array}{c} CH_3S \\ \phantom{CH_3}\diagdown \\ \phantom{CH_3SS}C=N-COOR^3 \\ \phantom{CH_3}\diagup \\ CH_3S \end{array} \quad (XIII)$$

wherein $R^3$ has the same meanings as defined above; or
c. a compound of the formula, $$\text{(benzimidazole with } N-R^1, \text{ 2-}NHR^2\text{)} \quad (XIV)$$

wherein $R^1$ and $R^2$ each have the same meanings as defined above, is reacted with a haloformate of the formula, $$X - COOR^3 \quad (XV)$$

wherein X and $R^3$ each have the same meanings as defined above; or
d. substituent Z of a compound of the formula $$\text{(benzimidazole, 2-}NH-COOR^3, N-(CH_2)_n-Z\text{)} \quad (XVI)$$

wherein $R^3$ and n each have the same meanings as defined above and Z stands for a leaving group replaceable by a sulfonic acid moiety, is replaced by a sulfonic acid moiety,
whereby a disclosed compound of the formula is obtained either directly or through intermediates, and, if desired, a disclosed compound of the formula is converted into its salts or quaternary salts, or is liberated from its salts.

Thus the new disclosed compounds of the formula can be prepared according to the invention by several alternative routes.

According to a preferred method of the invention a 2-benzimidazolecarbamic acid alkyl ester is reacted with a sulfone. As sultone reactant the widest variety of compounds, such as 1,3-propanesulfone, 1,4-butanesulfone, or 1,8-naphthonesulfone can be used.

As mentioned above, the disclosed compounds of the formula exist in two tautomeric forms. The compounds of the second tautomeric formula, owing to the presence of a basic group in the molecule, form intramolecular salts, thus their solution is neutral or near to neutrality. These solutions can be acidified or rendered alkaline without the formation of precipitate.

In practice it is very advantageous to use the disclosed compounds of the formula in the form of their salts. The calcium, magnesium, aluminum and alkali metal salts, as well as the salts formed with organic bases are, in general, readily water-soluble substances. If desired, the disclosed compounds of the formula can also be converted into their quaternary salts.

The invention relates further to a process for the preparation of biologically active compositions containing as active agent at least one compound according to the invention. These compositions can be prepared by methods known per se, thus, for example, by admixing the active agents with appropriate solid or liquid carriers and/or diluents. These compositions may contain, in addition to the disclosed compounds of the formula and/or the salts and/or quaternary salts thereof, other biologically active substances as well. Of these additional biologically active substances e.g. insecticidal, bactericidal, nematocidal, fungicidal, etc. agents, as well as other chemicals usable in the agriculture, such as substances promoting ripening, etc. are to be mentioned. Thus the compositions can also be used, in addition to the inhibition of plant mycosis, to other agricultural purposes. The activities of certain biologically active substances are potentiated synergistically in the presence of the new compounds according to the invention.

The 2-benzimidazolecarbamic acid alkyl ester derivatives containing an alkyl- or aralkyl-ω-sulfonic acid group or their salts can be used to great advantage as fungicidal and/or ovicidal agents in the form of aqueous solutions or solutions formed with water-miscible aqueous organic solvents. The aqueous solutions may contain the active ingredients in concentrations of 0.001 to 50 %.

The aqueous solutions of the active agents according to the invention, containing optionally a water-soluble organic solvent as well, can be prepared preferably by reacting a 2-benzimidazolecarbamic acid alkyl ester with a sultone suitably in the presence of an acid amide, particularly dimethylformamide, and diluting the obtained solution with water. This method provides an extremely simple way of preparation, since the formulation procedures, usually comprising several different steps as occurs in the production of similar compositions, can be completely omitted. According to a preferred method of the invention the reaction mixture is diluted to the desired concentration at the place of application, thereby reducing the costs of transportation.

The aqueous solutions of the new fungicidal and/or ovicidal agents according to the invention are extremely stable, and even upon prolonged storing no turbidity or, in the case of acid addition salts, hydrolysis occurs. This property of the new active agents is extremely important in practical application.

If desired, various additives, such as emulsifying agents, substances suppressing crystallization surfactants, etc. can be admixed with the aqueous solutions of the fungicidal and/or ovicidal agents according to the invention, the use of such additives is, however, not necessary. They are applied primarily when the composition also contains, in addition to the active agent according to the invention, other active ingredients, such as insecticidal, bactericidal, nematocidal or fungicidal agents or other agricultural chemicals, such as substances promoting ripening, etc.

The 2-benzimidazolecarbamic acid alkyl ester derivatives containing an alkyl-ω-sulfonic acid group can also be processed, apart from the solutions mentioned above, into other compositions, such as powder mixtures, pastes, pellets, etc. These compositions can be prepared by methods know in the art, e.g. by admixing the active agent with an appropriate carrier, such as talc, kaolin, chalk, etc. If desired, other additives, such as surfactants or dispersants, e.g. polyoxyethylene fatty alcohol esters, polyoxyethylene fatty acid ethers, alkyl and aryl sulfonates, lignin or sulfite waste liquor can also be used in the preparation of such compositions.

The active agents can be applied in themselves, in the form of compositions, or in the form of mixtures prepared from these compositions, such as solutions, emulsions, suspensions, dusts, pastes or pellets ready for use. These substances are applied to the plants in usual ways, such as by spraying, dusting, nebulizing or flooding.

The invention relates further to a method for combatting fungal diseases of plants, in which a disclosed compound of the formula and/or a salt and/or a quaternary salt thereof is applied onto the plant or onto the environment of the plant.

The compounds according to the invention can also be applied to cure plants already injured by fungal pests. In this instance a neutral, concentrated aqueous solution of a compound according to the invention is injected into the stem or roots of the injured plant. This method enables already injured plants to be treated and cured without applying prophylactive treatments requiring great amounts of active agent. Thus the expensive spraying equipments can be replaced optionally by a simple syringe. The invention is, however, not restricted to this special and completely novel way of combatting fungal diseases of plants, but also extends to all conventional agricultural operations provided that a disclosed compound of the formula and/or a salt and/or a quaternary salt thereof is applied.

The compounds according to the invention are prepared generally by reacting a 2-benzimidazolecarbamic acid alkyl ester with an alkyl sultone in the presence of an acid amide. According to a preferred method 2-benzimidazolecarbamic acid methyl ester is reacted with 1,3-propanesulfone in dimethylformamide at 100° to 152°C, preferably at 110° to 130°C. The thus-obtained solution is either utilized directly in the production of fungicidal and/or ovicidal compositions, or the water-soluble product, the derivative of 2-benzimidazolecarbamic acid methyl ester, containing the propyl-ω-sulfonic acid group, is precipitated with an appropriate solvent, such as acetone. This compound is soluble in water, and the pH of the aqueous solution is 5 to 7.

To investigate the fungistatic effect of the compounds according to the invention a barley malt culture medium solidified with 3 % of agar (pH = 6.0–6.2) is used. 50 ml. portions of the liquefied culture medium are filled into Petri dishes, and 1, 0.5, 0.25 or 0.1 ml., respectively, of the aqueous-alcoholic solution of the compound to be tested (dilution: 1:500) are added to the culture media. After homogenization the culture media contain the compound to be tested in concentrations of 1:25,000, 1:50,000, 1:100,000 and 1:250,000, respectively. The surfaces of the solidified culture media are inoculated with the test microorganisms, and the dishes are incubated at 28°C for 5 days. Thereafter the fungicidal effects of the tested compounds are evaluated. In the control, where aqueous alcohol containing no active agent is added to the culture media, no influence on the microorganism growth can be observed.

The results of the above test are summarized in Table 1.

Table 1

| Microorganism strain | Fungistatic activity/limiting dilution (ml) Compound | | |
|---|---|---|---|
| | 1 | 2 | 3 |
| Trichotheicium roseum | 4 | 4 | 4 |
| Fusarium oxysporum | 4 | 4 | 4 |
| Vericillium albo-atrum | 4 | 4 | 4 |
| Cladosporium herbarum | 4 | 4 | 4 |
| Septoria lycopersici | 4 | 4 | 4 |
| Ustilago maydis | 4 | 4 | 4 |
| Trichophyton gypseum | 4 | 4 | 10 |
| Trichophyton mentagrophytes | 4 | 4 | 4 |
| Trichophyton interdigitale | 4 | 4 | 4 |
| Trichophyton rubrum | 4 | 4 | 4 |
| Epidermophyton Kaufmann-Wolf | 4 | 4 | 10 |
| Achorion quickeanum | 4 | 4 | 10 |
| Penicillium funculosum | 2 | 2 | 2 |
| Penicillium simplicissimum | 2 | 2 | 2 |
| Aspergillus candidus | 2 | 2 | 2 |
| Aspergillus niger | 4 | 4 | 4 |

Compound 1: 1-butylcarbamoyl-2-benzimidazolecarbamic acid methyl ester

Compound 2: 2-benzimidazolecarbamic acid methyl ester

Compound 3: the derivative of 2-benzimidazolecarbamic acid methyl ester containing propyl-ω-sulfonic acid group Compound 3 has the following formula:

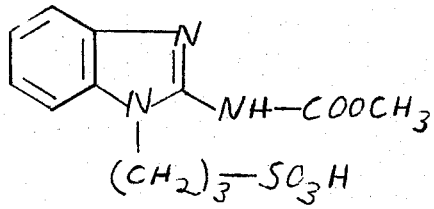

The phytotoxic activity of the derivative of 2-benzimidazolecarbamic acid methyl ester containing propyl-ω-sulfonic acid group is tested as follows:

The test is carried out on white mustard (Sinapis alba), accepted as one of the most sensitive dicotyledon. Petri dishes, 9 mm. in diameter, are filled with soil, about 50 seeds of white mustard are placed into each Petri dishes, and the seeds are covered with a layer of 2-3 mm. of vegetable soil. The cultures are watered with spring-water and maintained at 20° to 22°C. The seeds started to germinate, and reached a height of 2 to 2.5 cm. after 3 to 4 days. At this time one group of the test plants was sprayed with a 0.2 % or 0.1 % solution of the active agent, respectively, while in the other group the soil was sprinkled with 5 ml. per dish of the same aqueous solutions. No symptoms of phytotoxicity could be observed in either of the groups.

In order to obtain information on the acute toxicity of the new compounds towards warm-blooded animals, toxicity tests were carried out on rats. No toxic symptoms could be observed even in as high dosages as 100 mg./kg. body weight.

Compound 3 of Table 1 can be applied not only to combat fungal pests of plants, but it can also be used with good results for the treatment of fungal infections occurring on human skin. This is also evidenced by the data of Table 1, wherein some humanpathogeneous fungi are also included in the test microorganisms. Accordingly, this compound can also be applied for combatting the fungal diseases of human skin in the form of usual compositions, such as aqueous solutions, lotions, ointments, soaps, etc.

The invention is elucidated in detail by the aid of the following non-limiting Examples.

EXAMPLE 1

A mixture of 200 g. of 2-benzimidazolecarbamic acid ethyl ester and 400 ml. of dimethylformammide is heated to 80°C with stirring, and 150 g. of 1,3-propanesultone are added to the mixture. An exothermic reaction sets in, and the mixture warms to 120°C. The mixture is maintained at this temperature for 30 minutes, and small samples are removed periodically from the homogeneous mixture. The reaction terminates when the sample gives a clear solution also when diluted with water. The dimethylformamide solution contains 310 g. of the product. This solution can be used directly as plant protecting composition after diluting it to an appropriate concentration.

EXAMPLE 2

A mixture of 20 g. of 2-benzimidazolecarbamic acid methyl ester, 15 g. of 1,3-propanesultone and 40 ml. of dimethylformamide is heated to 110°-130°C with stirring. After 15 minutes of heating a homogeneous solution is obtained. The solution is heated for additional 15 minutes, then cooled to room temperature, and added dropwise to 600 ml. of cold (0°C) acetone with stirring. The separated product is filtered off and washed with acetone. After drying in vacuo at 50°C, the product weighs 30.5 g. Yield: 92.3 %; m.p.: 110°-112°C.

Analysis: calculated: C: 46.1 %, H: 4.85 %, N: 13.4 %, S: 10.05 %; found: C: 45.69 %, H: 5.03 %, N: 13.1 %, S: 9.67 %.

The product is unrestrictedly water-soluble, the pH of the aqueous solution is 6. The I.R. spectrum of the product differs to a great extent from that of the starting 2-benzimidazolecarbamic acid methyl ester, and contains characteristic bands at 1045 and 1760 cm$^{-1}$.

EXAMPLE 3

3.1 g. of the derivative of 2-benzimidazolecarbamic acid methyl ester containing the propyl-ω-sulfonic acid group are dissolved in 20 ml. of water, and 1 g. of copper(II)acetate hydrate is added to the solution. A deep green solution is obtained.

EXAMPLE 4

3.1 g. of the derivative of 2-benzimidazolecarbamic acid methyl ester containing the propyl-ω-sulfonic acid group are dissolved in 20 ml. of water, and 1.4 g. of methyl-ethylamine are added to the solution. The solution is filtered through activated carbon in order to remove the small amount of precipitate separated upon addition.

EXAMPLE 5

One proceeds as described in Example 1 with the difference that the obtained dimethylformamide solution is diluted to an active agent concentration of 80 p.p.m. A sprayable composition is obtained.

EXAMPLE 6

One proceeds as described in Example 1 with the difference that 50 % of calcium magnesium ligninsulfonate, 5 % of hydrated attapulgite and 8 % of anhydrous sodium carbonate are admixed with the dimethylformamide solution (all percentages are related to the amount of the active agent), and the mixture is diluted with water to an active agent concentration of 300 p.p.m. A sprayable composition is obtained.

EXAMPLE 7

One proceeds as described in Example 2. The obtained product is diluted with water to an appropriate concentration, and utilized as a sprayable composition. If desired, a wetting agent, such as an alkylsulfonate, polyglycol, methyl cellosolv, etc. can be admixed with the solution.

EXAMPLE 8

A powder mixture of the following composition is prepared:

| | |
|---|---|
| product of Example 2 | 25 to 50 % |
| filling agent (e.g. talc, kaoline, chalk, etc.) | 50 to 75 % |
| methylcellulose | 0.1 to 0.5 % |
| sodium alkylnaphthalenesulfonate | 2 to 3 % |

What is claimed is:

1. A compound of the formula:

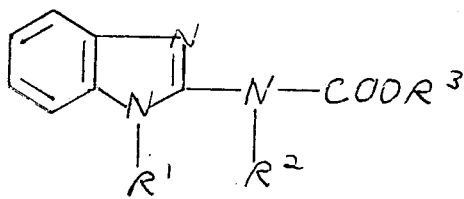

wherein $R^1$ and $R^2$ each is hydrogen or $-(CH_2)_n-SO_3H$ with at least one of $R_1$ and $R_2$ being $-(CH_2)_n-SO_3H$;

$n$ is an integer between 1 and 5; and $R^3$ is alkyl, or a fungicidally acceptable salt thereof.

2. A fungicidal composition containing a compound or fungicidally acceptable salt thereof as defined in claim 1 in a fungicidally effective amount in a suitable inert carrier.

3. The composition defined in claim 2 wherein the fungicidally acceptable salt is a calcium salt, magnesium salt, aluminum salt, copper salt or alkali metal salt.

4. The composition defined in claim 2 which also contains a watermisicible solvent.

5. A process for combatting fungal disease in plants in which the compound or fungicidally acceptable salt thereof defined in claim 1 is applied directly to the plant in a fungicidally effective amount for a period of time sufficient to ameliorate the fungal disease.

6. A process for combatting fungal disease in plants in which a compound or fungicidally acceptable salt thereof defined in claim 1 is applied to the environment in the vicinity of the plant in a fungicidally effective amount for a period of time sufficient to ameliorate the fungal disease.

* * * * *